(12) United States Patent
Lumgair et al.

(10) Patent No.: US 6,870,072 B2
(45) Date of Patent: Mar. 22, 2005

(54) HEAT RECOVERY IN AN OLEFIN PRODUCTION PROCESS

(75) Inventors: David R Lumgair, Craddockville, VA (US); James Harding Beech, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 255 days.

(21) Appl. No.: 10/020,732

(22) Filed: Oct. 30, 2001

(65) Prior Publication Data

US 2003/0088136 A1 May 8, 2003

(51) Int. Cl.[7] ................................................. C07C 1/20
(52) U.S. Cl. ........................ 585/639; 585/634; 585/640; 585/910; 585/911; 208/161
(58) Field of Search ................. 585/634, 639, 585/640, 910, 911; 208/161

(56) References Cited

U.S. PATENT DOCUMENTS

| | | | |
|---|---|---|---|
| 4,338,475 A | 7/1982 | Pennington et al. | 585/408 |
| 4,499,327 A | 2/1985 | Kaiser | 585/640 |
| 4,935,568 A | 6/1990 | Harandi et al. | 585/300 |
| 5,264,645 A * | 11/1993 | Hugues et al. | 585/640 |
| 5,302,775 A | 4/1994 | Hugues et al. | 585/639 |
| 5,744,680 A * | 4/1998 | Mulvaney et al. | 585/640 |
| 5,990,369 A * | 11/1999 | Barger et al. | 585/640 |
| 6,121,504 A | 9/2000 | Kuechler et al. | 585/640 |
| 6,166,282 A | 12/2000 | Miller | 585/638 |
| 6,403,854 B1 * | 6/2002 | Miller et al. | 585/638 |
| 6,459,009 B1 * | 10/2002 | Miller et al. | 585/809 |
| 6,482,998 B1 * | 11/2002 | Kuechler et al. | 585/638 |
| 2002/0087041 A1 * | 7/2002 | Kuechler et al. | 585/638 |

OTHER PUBLICATIONS

Zenz, F.A. and D. F. Othmer, "Riser Reactor," *Fluidization and Fluid–Particle Systems*, pp. 48–59, Reinhold Publishing Corp., NY 1960.

* cited by examiner

*Primary Examiner*—Walter D. Griffin (57) ABSTRACT

Disclosed is a process for recovering heat in an oxygenate to olefin ("OTO") production process. The process includes removing heat while maintaining the temperature of an effluent stream that comprises solid particles (typically catalyst particles) and a gas phase comprising prime olefins from an OTO reactor above the dew point temperature of the effluent stream. The process further includes washing the effluent stream in solids wash to remove the solid particles from the gas phase into a liquid wash medium.

44 Claims, 1 Drawing Sheet

Figure 1

HEAT RECOVERY IN AN OLEFIN PRODUCTION PROCESS

FIELD OF THE INVENTION

This invention relates to producing and recovering olefins from an oxygenate feed stream and more particularly to heat recovery in the process of producing and recovering olefins from an oxygenate feed stream.

BACKGROUND OF THE INVENTION

Prime olefins, defined as ethylene and propylene and are materials that are used to make polyolefins. Specifically, ethylene and propylene are used to make polyethylene polypropylene respectively—two of the most commonly used plastics. These prime olefins are produced by taking larger hydrocarbons (e.g., C6 to C8 hydrocarbons) found in petroleum feed stream and subjecting it to steam cracking or catalytic cracking. Cracking processes break apart these larger hydrocarbons into smaller olefins including ethylene and propylene. However, the cracking process produces nitrogen and sulfur impurities that require expensive purification steps.

Another process for producing higher olefins is the process known as an oxygenate to olefin process ("OTO") process. The OTO process takes an oxygenate feed stream and converts it to ethylene and propylene. The OTO process generally includes no sulfur and nitrogen impurities and permits the use of a methanol feed stream produced from natural gas. Consequently, alcohol, alcohol derivatives, and other oxygenates have promise as an economic non-petroleum source for prime olefin production. Nonetheless, effluent from the OTO process comprises olefins with hydrocarbon oxygenates and high levels of water vapor. Accordingly, the recovery of olefins from an OTO process involves unique technical challenges.

U.S. Pat. No. 4,499,327 discloses making olefins from methanol using any of a variety of SAPO molecular sieve catalysts. The type of reactor disclosed is a fluid bed reactor where upward flow of vapors through the catalyst causes catalyst to be fluidized and to be carried by the flow of vapor. Consequently, catalyst often becomes entrained in an olefin effluent stream leaving the reactor.

U.S. Pat. No. 4,338,475 discloses a process for converting methanol to olefins where the catalyst is separated from the effluent stream by cyclone separators (or "cyclones") in the reactor. Then, the catalyst is returned, directly or indirectly to the reactor. However, the flow of the catalyst through the reactor, cyclone separators, and other equipment in contact with circulating catalyst, subjects the catalyst to great mechanical stresses. The stressed catalyst tends to disintegrate during the process to produce dust-like particles, commonly referred to as catalyst fines. As defined herein, catalyst fines are catalyst particles whose greatest dimension is less than $30\mu$. Due to their small size and weight, catalyst fines are not efficiently removed by the cyclone separators (or cyclones) within the reactor. Consequently they become entrained (or suspended) in the effluent stream from the reactor. The smaller the catalyst fines, the more difficult they are to remove by conventional processes.

Removing catalyst particles in the effluent stream is taught in U.S. Pat. No. 4,935,568 (the 568 patent). The 568 patent discloses a process for preparing hydrocarbons from an oxygenate feed stream in which catalyst fines are recovered from an effluent stream by use of cyclone separators and/or sintered metal filter systems. Catalyst particles, particularly fines that are entrained with the gaseous effluent stream, make filter systems, including sintered metal filter systems, impractical. Filter elements may quickly become blocked with catalyst particles and need to be cleaned or replaced. Expensive and sophisticated filter systems, which provide for some measure of on-line cleaning, or low efficiency filters that allow a substantial portion of solids through, are typically required to provide improvements to this problem.

One OTO system is illustrated in U.S. Pat. No. 6,121,504 (the 504 patent). In the 504 patent, an oxygenate to olefin reactor produces an effluent stream. The effluent stream passes through heat exchangers for the efficient recovery of heat. Then the effluent stream passes through a quench tower. The 504 patent provides no guidance on how to manage the catalyst particles that exit the reactor entrained with the gaseous effluent stream.

Catalyst particles and other solids that leave the reactor suspended in the effluent stream from an OTO reactor pose a particular problem in the overall OTO process. These catalyst particles sometimes fall out of the gaseous effluent stream and deposit on downstream equipment in a phenomenon known to those skilled in the art as fouling. Fouling is the accumulation of solid deposits on surfaces of the recovery train of a reactor such as an OTO reactor. In conduits, fouling is believed to significantly decrease the cross sectional area for fluid flow, increasing pressure drop through the conduit and decreasing process efficiency. On heat exchangers, fouling is believed to occur on heat transfer surfaces such as tubes or fins, which increases the thermal resistance of those surfaces and causes the heat exchanger to become less efficient. Typically, this loss of efficiency negatively impacts the operability of the OTO reactor and other downstream equipment in the recovery train. To avoid this loss of efficiency or restore operability, various equipment items typically need to be shut down and cleaned, perhaps necessitating the shutdown of the entire OTO system.

Therefore, a need exists for an effective process for operating an OTO process to reduce the accumulation of catalyst particles in the OTO recovery train, and thereby reduces fouling. The present invention satisfies these and other needs.

SUMMARY OF THE INVENTION

The present invention is a process for controlling accumulation of catalyst solids in the recovery train of the oxygenate to olefin process. The process comprises providing an effluent stream from an oxygenate to olefin reaction. The effluent stream comprises solid particles and a gas phase. The gas phase contains prime olefins and has a dew point. The process also comprises removing heat from the effluent stream while maintaining a temperature of the gas phase above the dew point during the step of removing heat. Additionally, the process also includes washing the effluent stream in a solids wash to remove solid particles from effluent stream into a wash medium.

In one embodiment, the process is as stated above. Additionally, the effluent stream comprises water and hydrocarbons and has an aqueous dew point and a non-aqueous dew point, the aqueous dew point being higher than the non-aqueous dew point. In another embodiment, the step of removing heat comprises removing heat with one or more heat exchanger. In yet another embodiment, the oxygenate to olefins reaction occurs in a reactor. The reactor is in fluid communication with the one or more heat exchangers and the solids wash by a conduit. Thus, the effluent stream flows from the reactor through the conduit to the heat exchangers and then via the conduit to the quench.

In another embodiment the process additionally comprises providing a feed stream to the oxygenate to olefin reactor. The feed stream is used as a cooling fluid in the heat exchanger. In another embodiment, the cooling fluid is boiled within the heat exchanger. In yet another embodiment, the wash medium is water. In still another embodiment, the solids wash is a quench tower.

In another embodiment, there is a process for producing olefins. The process comprises providing an oxygenate feed stream. The oxygenate feed stream is reacted in the presence of a catalyst to produce an effluent stream. The effluent stream has a dew point and comprises an olefin containing gas phase and catalyst solids. Heat is removed from the effluent stream while maintaining the temperature of the effluent stream above the dew point. The effluent stream is then contacted with a liquid to separate the catalyst solids from the olefin containing gas phase.

According to one embodiment, the catalyst is a molecular sieve catalyst. In another embodiment the step of contacting occurs in a quench tower. The step of removing heat is accomplished using a heat exchanger. The oxygenate feed stream is used as a cooling fluid in the heat exchanger. In another embodiment, the oxygenate feed is boiled in the step of removing heat.

In yet another embodiment of the present invention, there is a process for producing olefins. The process comprises providing an oxygenate feed stream. The oxygenate feed stream is reacted in the presence of a catalyst to produce an effluent stream. The catalyst is separated from the effluent stream in a cyclone separator to produce an effluent stream having a temperature and comprising an olefin containing gas phase and catalyst fines. Heat is then removed from the reactor effluent, while maintaining the temperature above the dew point of the effluent stream during the step of removing heat to provide a cooled effluent stream. Finally, the catalyst fines are washed from the effluent stream in a solids wash to remove solids This invention will be better understood with reference to the Detailed Description of the Invention together with the drawings and examples, which are intended to illustrate specific embodiments within the overall scope of the invention as claimed and are not provided by way of limitation of the claimed invention.

DETAILED DESCRIPTION OF THE INVENTION

It has been found that solid phase particles entrained in the gaseous effluent stream from an OTO reactor, such as catalyst or other particles, will not accumulate in the recovery train located downstream from the OTO reactor, or will accumulate at very low rates that do not necessitate frequent shutdown of equipment, if the gaseous effluent stream leaving the OTO reactor is kept above its dew point temperature until it reaches a solids wash, such as a quench device. Thus, none of the components in the gaseous reactor effluent is condensed to form a liquid in any elements in the recovery train prior to the gaseous effluent stream reaching a solids wash. The recovery train is herein defined as all equipment and conduits, including any heat exchangers and solids wash devices, through which at least a portion of the gaseous effluent stream from an OTO flows. The boundary of the OTO reactor is herein defined as the gas phase exit of the last solids separation device through which the gaseous effluent stream flows, typically a cyclone separator, or in other embodiments, a filter. The OTO process is herein defined as the OTO reactor and regenerator, oxygenate feed system, recovery train, and all other elements required to make olefins from oxygenates, and recover, separate and purify various olefin streams present in the OTO reactor effluent stream.

A solids wash (or solids wash device) is defined, for purposes herein, as a device in an effluent stream that is configured to contact solid phase particles suspended in the gas phase of an effluent stream with a sufficient quantity of liquid to remove solid phase particles from the gas phase into the liquid. The washing of the solids from the effluent stream prevents accumulation of catalyst particles and other solids in the recovery train downstream from the solids wash by transferring the solids to a dilute liquid phase that flows freely through conduits and equipment.

Without being constrained to a particular theory or mechanism of action, accumulation of solid phase particles (or solids) is believed to be caused when the solids in the effluent stream contact small quantities of liquid components, including condensed components from the gaseous effluent stream, forming mud on the surfaces of equipment downstream of the OTO reactor. These small quantities of liquid components tend to pull the solids into the liquid phase due to surface tension effects, thus forming mud. When small quantities of liquid components, e.g., condensed components from the gaseous effluent stream, are present in such equipment as a conduit or heat exchanger, at or below the dew point temperature of the gaseous effluent stream, heat is incrementally removed along the length of their surfaces. Thus, the present invention permits the reaction effluent to be cooled without forming mud in the recovery train. OTO process equipment downtime and inefficient operation of such equipment are avoided.

The following is a description of the process of the present invention including the selection of the catalyst, operation of the OTO reactor, and catalyst fines recovery.

The Catalyst

According to one embodiment of the invention, the process is for recovery of catalyst fines from the OTO process. Catalysts known for converting oxygenate to olefins are known in the art. According to an embodiment, a preferred catalyst for converting oxygenate to olefins is one that incorporates a silicoaluminophosphate (SAPO) molecular sieve. Silicoaluminophosphate molecular sieves include but are not limited to the group comprising SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred catalysts, according to this embodiment, are SAPO-18, SAPO-34, SAPO-35, SAPO-44, and SAPO-47, particularly SAPO-18 and SAPO-34, including the metal containing forms thereof and mixtures thereof As used herein, the term mixture is synonymous with combination and is considered a composition of matter having two or more components in varying proportions, regardless of their physical state.

The silicoaluminophosphate molecular sieves typically produced are very small and are therefore typically admixed (i.e., blended) with other materials to produce catalyst particles of the desired size. These other materials that are blended with the molecular sieve typically include various inert or catalytically inactive materials and various binder materials, including compositions such as kaolin and other clays, various forms of rare earth metals, metal oxides, other zeolite catalyst components, zeolite catalyst components, alumina or alumina sol, titania, zirconia, magnesia, throia, beryllia, quartz, silica or silica sol, aluminum chorhydril, and mixtures thereof. The blended composition is typically mixed with a substantial quantity of a liquid such as water, with the resulting slurry subjected to a process known to those skilled in the art as spray drying. In spray drying, small catalyst particles are formed in an atomizing nozzle, and partially dried so they maintain a substantially spherical shape.

When blended, the resulting composition is referred to as a SAPO catalyst, a catalyst comprising the SAPO molecular sieve. The catalyst particles should be of sufficient size to allow removal by conventional cyclones, but not so large that they are not easily fluidized. The catalyst composition, according to one embodiment, comprises about 1% to about 99%, more preferably from about 5% to about 90%, and most preferably from about 10% to about 80%, by weight of molecular sieve. A wide range of catalyst particle sizes are useful according to one embodiment of the present invention. According to an embodiment, the catalyst composition provided to an oxygenate to olefin reactor has a particle size, typically expressed as the largest dimension of the particle, or range of sizes, of from about 30 $\mu$m to about 3,000 $\mu$m, more preferably from about 30 $\mu$m to about 200 $\mu$m most preferably from about 40 $\mu$m to about 150 $\mu$m.

The molecular sieve or catalyst, according to another embodiment, is subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof. While such treatment can increase the hardness of a catalyst, it does not eliminate the production of catalyst fines in the effluent stream.

The OTO Reaction

The invention according to one embodiment is management of solid phase particles in the recovery train of an OTO reaction according to the principles set forth herein. Accordingly, the OTO reaction is explained as follows. In the OTO reaction, the feed stream containing an oxygenate, and optionally a diluent or a hydrocarbon added separately or mixed with the oxygenate, is contacted with the catalyst, in the OTO reactor.

Suitable reactor types include conventional reactors such as fixed bed reactors, fluid bed reactors, and riser reactors. These and other types of conventional reactors are described in Fluidization Engineering, D. Kunii and O. Levenspiel, Robert E. Krieger Publishing Co. NY, 1977. According to one embodiment, preferred reactors are riser reactors. Conventional riser reactor designs are further described in "Riser Reactor," Fluidization and Fluid-Particle Systems, pages 48–59, F. A. Zenz and D. F. Othmer, Reinhold Publishing Corp., NY 1960, the description of which is incorporated herein by reference.

The oxygenate feed stream of this invention comprises at least one organic compound that contains at least one oxygen atom, such as aliphatic alcohols, ethers, carbonyl compounds (aldehydes, ketones, carboxylic acids, carbonates, esters and the like). In embodiments where the oxygenate is an alcohol, the alcohol optionally includes an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: alcohols such as methanol, ethanol, n-propanol, isopropanol, and $C_4$–$C_{20}$ alcohols; ethers such as methyl ethyl ether, dimethyl ether, diethyl ether, di-isopropyl ether; and other oxygenates such as formaldehyde, dimethyl carbonate, dimethyl ketone, and acetic acid. According to another embodiment, the composition comprises mixtures of all the foregoing oxygenates in various proportions. According to another embodiment, preferred oxygenate compounds are methanol, dimethyl ether, or a mixture thereof.

According to one aspect of the invention, one or more inert diluents are present in the feed stream. According to another aspect, the amount of diluent is from 1 to 99 molar percent, based on the total number of moles of all feed and diluent components fed to the reactor (or catalyst). As defined herein, diluents are compositions that are essentially non-reactive across a molecular sieve catalyst, and primarily function to make the oxygenates in the feed stream less concentrated. Typical diluents include, but are not necessarily limited to helium, argon, nitrogen, carbon monoxide, carbon dioxide, water, essentially non-reactive paraffins (especially the alkanes such as methane, ethane, and propane), alkylenes, aromatic compounds, and mixtures thereof. The preferred diluents, according to one embodiment, are water and nitrogen. According to one process for using a diluent, water is injected in either liquid or vapor form.

According to one embodiment, the reactor is supplied with a feed stream comprising oxygenate compounds. The oxygenate feed stream is contacted with a molecular sieve catalyst at a weight hourly space velocity (WHSV) of about 1 hr$^{-1}$ or more. According to another embodiment, the weight hourly space velocity is preferably in the range of from about 1 hr$^{-1}$ to about 1000 hr$^{-1}$, more preferably in the range of from about 20 hr$^{-1}$ to about 1000 hr$^{-1}$, and most preferably in the range of from about 20 hr$^{-1}$ to about 500 hr$^{-1}$. WHSV is defined herein as the weight of oxygenates in the feed stream per hour per weight of the molecular sieve content of the catalyst. Optionally, WHSV is defined as the weight of oxygenate plus hydrocarbons in the feed stream per hour per weight of the molecular sieve content of the catalyst when so specified. Because the catalyst or the feed stream optionally contains other materials that act as inerts or diluents, the WHSV is calculated on the weight basis of the oxygenate feed (alternatively oxygenate and hydrocarbons) that are present, and the molecular sieve contained in the catalyst.

According to one embodiment, the oxygenate feed is contacted with the catalyst when the oxygenate is in a vapor phase. In another embodiment, the process is carried out in a liquid or a mixed vapor/liquid phase. When the process is carried out in a liquid phase or a mixed vapor/liquid phase, different conversion and selectivity of feed-to-product results therefrom, depending upon the catalyst and reaction conditions.

According to an embodiment, the OTO process is carried out using a wide range of temperatures. A typical temperature range is from about 200° C. to about 700° C. According to one embodiment, the temperature of the reactor ranges from about 300° C. to about 600° C., preferably from about 350° C. to about 550° C. The pressure varies over a wide range, including autogenous pressures. According to one embodiment, oxygenate partial pressures is about 1 psia (6.9 kPa) or greater, preferably about 5 psia (34 kPa) or greater. The process is particularly effective at higher oxygenate partial pressures. Accordingly an oxygenate partial pressure of about 20 psia (140 kPa) or greater is preferred in one embodiment. In another embodiment, the oxygenate partial pressure is preferably about 25 psia (170 kPa) or greater, more preferably about 30 psia (200 kPa) or greater. For practical design purposes, the oxygenate partial pressure is about 500 psia (3400 kPa) or less in one embodiment. Preferably, the partial pressure of the oxygenate is about 400 psia (2800 kPa) or less in this embodiment and most preferably about 300 psia (2000 kPa) or less.

During operation of at least one embodiment of the invention, hydrocarbons accumulate on the catalyst, which renders the catalyst substantially ineffective. This buildup of hydrocarbons on the catalyst is called "catalyst coking." According to one process of this invention, coked catalyst is regenerated by contacting it with a regeneration medium to remove all or part of the coke deposits on the catalyst. In some cases, this regeneration occurs periodically within the reactor by ceasing the flow of feed stream to the reactor, introducing a regeneration medium, ceasing flow of the regeneration medium, and then reintroducing the feed stream to the fully or partially regenerated catalyst. Regeneration occurs either periodically or continuously. Typically, regeneration occurs outside the OTO reactor by removing a portion of the deactivated catalyst to a separate regenerator, regenerating the coked catalyst in the regenerator, and subsequently reintroducing the regenerated catalyst to the reactor. Regeneration occurs at times and conditions appropriate to maintain a desired level of coke on the entire catalyst within the reactor.

To make up for any catalyst loss during the regeneration or reaction process, fresh catalyst is added according to one embodiment. Particularly, the fresh catalyst is added to the regenerator, where it proceeds along with the regenerated catalyst to the reactor. According to another embodiment, fresh catalyst is added to the reactor independent of the regenerated catalyst.

Catalyst Fines Recovery

The present invention produces an effluent stream that contains prime olefins and other byproducts. The effluent stream leaves the reactor in a gaseous state that is absent any liquid phase. According to one embodiment, the amount of prime olefins is about 40 wt % or more of the effluent stream excluding water and solid particles (e.g., catalyst particles). According to another embodiment, the amount of prime olefins in the effluent stream is about 45 wt % or more. In yet another embodiment, the amount of prime olefins in the effluent stream is about 50 wt % or more, and in still another embodiment, about 60 wt % or more excluding water and solid particles (e.g., catalyst particles).

According to one embodiment, the amount of ethylene in the effluent stream is about 20 wt % or more excluding water and solid particles (e.g., catalyst particles). According to another embodiment, the amount of ethylene in the effluent stream is from about 20 wt % to about 70 wt % excluding water and solid particles (e.g., catalyst particles).

According to one embodiment, the amount of propylene in the effluent stream is about 20 wt % or more excluding water and solid particles (e.g., catalyst particles). According to another embodiment, the amount of propylene in the effluent stream is from about 20 wt % to about 50 wt % excluding water and solid particles (e.g., catalyst particles).

According to one embodiment, the amount of byproducts (defined as chemicals produced from the OTO process other than prime olefins, water, or solid particles (e.g., catalyst particles) in the effluent stream is about 25 wt % or less excluding water and solid particles (e.g., catalyst particles). According to another embodiment, the amount of byproducts in the effluent stream is from about 4 wt % to about 25 wt %, in yet another embodiment, from about 5 wt % to about 20 wt %, excluding water and solid particles (e.g., catalyst particles).

The effluent stream of one embodiment contains a large quantity of water vapor along with olefin products. According to one embodiment, the effluent stream from the OTO reactor contains about 25 wt % or more water. In another embodiment, it contains from about 40 wt % to about 80 wt % water, and in yet another embodiment, it contains from about 50 wt % to about 65 wt % water.

The effluent of the OTO reactor stream of one embodiment contains some oxygenated hydrocarbons, including any non-reacted oxygenated feed. Furthermore, oxygenated hydrocarbons that are byproducts of the OTO reaction remains in the effluent stream. According to one embodiment, the amount of oxygenated hydrocarbons in the effluent stream range from about 0.2 wt % to about 30 wt % of the effluent stream excluding water and solid particles (e.g., catalyst particles).

The oxygenate hydrocarbons of this invention comprises at least one organic compound that contains at least one oxygen atom, such as aliphatic alcohols, ethers, carbonyl compounds (aldehydes, ketones, carboxylic acids, carbonates, esters and the like). In embodiments where the oxygenate hydrocarbon is an alcohol, the alcohol optionally includes an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenated hydrocarbons include, but are not limited to: alcohols such as methanol, ethanol, n-propanol, isopropanol, and $C_4$–$C_{20}$ alcohols; ethers such as methyl ethyl ether, dimethyl ether, diethyl ether, di-isopropyl ether; and other oxygenates such as formaldehyde, dimethyl carbonate, dimethyl ketone, and acetic acid. According to another embodiment, the composition comprises mixtures of all the foregoing oxygenates in various proportions.

The present invention will function with a wide range of solid particles (e.g., catalyst particles, present in the reactor effluent. In one embodiment, the reactor effluent contains about 0.15 wt % or less of solid particles (e.g., catalyst particles). In other embodiments, the gaseous reactor effluent contains about 0.10 wt % or less solid particles, or about 0.050 wt % or less solid particles, or about 0.025 wt % or less solid particles, or about 0.010 wt % or less of solid particles (e.g., catalyst particles). In an alternative embodiment, the gaseous reactor effluent contains about 0.001 wt % or more solid particles (e.g., catalyst particles), and in other alternative embodiments, the gaseous reactor effluent contains from about 0.001 wt % to about 0.15 wt % solid particles, or from about 0.003 wt % to about 0.10 wt %, or from about 0.005 wt % to about 0.05 wt % solid particles, or from about 0.005 wt % to about 0.025 wt % of solid particles (e.g., catalyst particles).

In another embodiment, the solid particles in the reactor effluent comprise about 50 wt % or more catalyst fines. In yet another embodiment, the solid particles in the reactor effluent comprises 75 wt % or more catalyst fines. In still another embodiment, the solid particles in the reactor effluent comprises 90 wt % or more catalyst fines.

According to one embodiment, the overall content and particle size distribution of solid particles suspended in the gaseous reactor effluent is effected by design and operation of cyclones and other catalyst recovery devices in the oxygenate conversion reactor of the present invention. Such design and operation techniques are well known to those skilled in the art. Other solid particles, in some cases, include but are not limited to metals or refractory components (e.g., fired bricks of silica or clay). These components comprise the materials from which the reactor is constructed. They are created by erosion of the reactor. Particularly but without limitation, the erosion occurs when the flowing catalyst particles contact the equipment.

In one embodiment of the present invention, heat is removed from the effluent stream after it leaves the OTO reactor prior to the entrance of a solids wash. The removal of heat from the effluent stream will cause its temperature to decrease. Heat removal occurs without limitation in conduits, heat exchangers, or other equipment in the OTO recovery train.

The problem of catalyst fouling is somewhat unique to the OTO process versus other methods of producing olefins because of the relatively large amount of water vapor in the effluent stream combined with the use of a fluidized catalyst. Water has a higher condensation temperature than most hydrocarbons made in an OTO reaction (including non-aromatic hydrocarbons containing up to 7 carbon atoms). Particularly, the majority of those made using small pore SAPO catalysts, which when combined with the partial pressures of water in an effluent stream, typically makes water the first compound to condense from the effluent stream as temperature is gradually reduced. Further, water has a higher heat of vaporization than most hydrocarbons.

In the OTO process, water is likely to be the first gas phase component in the effluent stream to condense. It typically condenses at the highest temperature relative to the other components. Water initially condenses from the reactor effluent when its dew point temperature is reached. In one example, the initial liquid droplets form on the surface of a heat exchanger contains most of the solids that were formerly entrained in the reactor effluent. If the quantity of liquid at a given point is low, and hence the concentration of solids in that liquid high, mud forms on the surfaces. Additionally, initial condensation is sometimes nucleated in the vapor phase by the solid particles. Liquid droplets forming in the vapor phase of the effluent stream will subsequently fall on or otherwise attach themselves to the surfaces of equipment. Mud formation is likely when liquid droplets absorb or contain a high concentration of solids.

The formation of the mud is prevented, according to one embodiment of the invention, if the temperature of the effluent stream is maintained above its dew point temperature prior to entering a solids wash. For the purposes of this application, the dew point temperature is defined as the temperature at which condensation of any of the components in the gaseous reactor effluent stream first begins. The dew point temperature is pressure dependent. As the pressure of the reactor effluent stream is increased the dew point temperature will increase.

The dew point temperature is also composition dependent. Because water and hydrocarbon typically form two phases, an effluent stream containing water and hydrocarbon will sometimes have two dew points—an aqueous dew point and a non-aqueous dew point. The aqueous dew point is the temperature at which aqueous phase first condenses. The non-aqueous dew point temperature is the temperature at which non-aqueous (hydrocarbon) phase first condenses. Dew point temperatures are a function of the partial pressure of the water and the hydrocarbons in the gas phase of the effluent stream.

The aqueous dew point temperature increases when water concentration increases, and similarly, the non-aqueous dew point temperature increases as the hydrocarbon partial pressure increases. The determination of the dew point temperature or temperatures of a particular composition is determined readily, by calculation or measurement or both, through employing techniques well known to those skilled in the art. Herein, the terms "dew point" and "dew point temperature" are synonymous. When a particular composition has both an aqueous and a non-aqueous dew point, it is understood that the term "dew point" or "dew point temperature" unless specified otherwise refers to the highest of the aqueous and non-aqueous dew point temperatures.

Depending on the catalyst, feedstock, and operating conditions utilized in the present invention, quantities of hydrocarbons having a normal boiling point greater than water is present in the gaseous reactor effluent according to one embodiment. In another embodiment, the reactor effluent (excluding water and catalyst particles) contains no more than about 10 wt % of components with a normal boiling point greater than water excluding water and catalyst particles. In another embodiment, the reactor effluent (excluding water and catalyst particles) contains about 5 wt % of components or more with a normal boiling point greater than water, and in still another embodiment, the reactor effluent (excluding water and catalyst particles) contains about 2 wt % or less of components with a normal boiling point greater than water. The condensation of small quantities of hydrocarbon is believed to cause the accumulation of solids and the formation of mud, in ways similar to the way described above for water. In one embodiment, the prevention of accumulation of solids is similarly prevented by the method of the present invention.

Accordingly, the gaseous effluent stream from the OTO reactor is at a temperature above its dew point. According to an embodiment, the temperature of the gaseous effluent stream is greater than or equal to about 200° C. According to one embodiment of the invention, the gaseous effluent stream has a temperature ranging from about 200° C. to about 700° C. In another embodiment, the temperature of the gaseous effluent stream ranges from about 300° C. to about 600° C. In yet another embodiment, the temperature of the gaseous effluent stream ranges from about 350° C. to about 550° C.

Conduits are used to convey the effluent stream to a solids wash. Conduits sometimes provide significant heat removal from the effluent stream due to exposure to the ambient environment (typically termed "heat loss"), causing the temperature of the effluent stream to decrease. Such conduits further include other elements, including but not limited to measurement devices, such as orifice plates to measure flow, or flow control devices, such as automated valves, or other elements and equipment items as may be found in an OTO recovery train. Control of the temperature decrease in a conduit is a function of appropriate design of conduit geometry and insulation, among other things, and is well known to those skilled in the art.

Heat exchangers are used downstream from the OTO reactor in one embodiment of this invention to remove heat from the effluent stream while conveying the effluent stream to a solids wash, and thus recover the heat energy produced in the exothermic OTO reaction. The effluent stream is cooled, reducing its temperature, by transferring heat to another fluid, whose temperature is increased. However, if the temperature of the effluent stream is allowed to drop below its dew point within the heat exchanger, mud is likely to form. According to another embodiment of the invention, the amount of heat removed from the heat exchanger is controlled such that the temperature of the effluent in the heat exchanger, the conduit or any other component of the OTO recovery train prior to the solids wash does not fall below the dew point temperature.

Control of the temperature decrease in a heat exchanger is a function of appropriate design of heat exchanger geometry and metallurgy, and fluid input and output thermal properties such as heat capacity, among other things, and is well known to those skilled in the art. According to one embodiment, the gaseous effluent stream is cooled by exchange with the feed stream of the OTO reactor or another fluid in a heat exchanger in the effluent stream. In a typical heat exchanger, heat is transferred from a hot fluid to a cold fluid through a solid surface or "wall" that separates the two fluids (typically referred to as "indirect heat transfer"). If the wall temperature on the hot or gaseous effluent side of the heat exchanger falls below the dew point temperature of the effluent stream, condensation occurs and mud accumulates in the heat exchanger. The wall temperature will be equal to or warmer than the temperature of the cooling fluid. Accordingly, by controlling the temperature of the cooling fluid, the wall temperature and temperature of the gas effluent stream can be controlled.

According to one embodiment of the present invention, the effluent stream is kept above its dew point in a heat exchanger, conduit or other equipment prior to entering a solids wash. In another embodiment, the effluent stream is kept at a temperature of about 1° F. (0.5° C.) or more above its dew point in a heat exchanger prior to entering a solids wash. In another embodiment, the effluent stream is kept at a temperature of about 5° F. (3° C.) or more above its dew point in a heat exchanger prior to entering a solids wash, and in yet another embodiment, the effluent stream is kept at a temperature of about 10° F. (5.5° C.) or more above its dew point in a heat exchanger prior to entering a solids wash.

Optionally, the present invention functions with the effluent stream from an OTO reactor being conveyed by a conduit to one or more heat exchangers. In one embodiment, the temperature decrease through this conduit from the OTO reactor to a heat exchanger does not exceed 50° F. (10° C.) while still being maintained above the dew point of the effluent stream. In another embodiment, the temperature decrease through this conduit from the OTO reactor to a heat exchanger does not exceed 20° F. (7° C.) while still being maintained above the dew point of the effluent stream.

Optionally, the effluent stream exits a heat exchanger and is conveyed to a solids wash via a conduit. In one aspect of the present invention, the temperature decrease in such a conduit from the exit of a heat exchanger to a solids wash is no greater than about 50° F. (28° C.) while still being maintained above the dew point of the effluent stream prior to entering the solids wash. In another aspect of the present invention, the temperature decrease in such a conduit from the exit of a heat exchanger to another heat exchanger or a solids wash is no greater than about 20° F. (11° C.) while still being maintained above the dew point of the effluent stream.

In one embodiment, the temperature of the cooling fluid is maintained such that it does not fall below the dew point temperature of the effluent stream. Thus, the wall temperature on the effluent side of the exchanger will also be maintained above the dew point temperature of the effluent stream. Optionally, the cooling fluid is selected under conditions such that it is maintained at its boiling temperature in the heat exchanger. In another alternative, this boiling temperature of the cooling fluid in the heat exchanger is at or above the dew point temperature of the effluent stream in the heat exchanger.

In the method of present invention, the effluent stream is conveyed, while undergoing heat removal and maintaining a temperature above its dew point temperature until it reaches the solids wash. Thus, the effluent stream enters the solids wash at a temperature above its dew point temperature. In one aspect of the present invention, the temperature of the effluent stream entering a solids wash is about 1° F. (0.5° C.) or more above the dew point temperature of the effluent stream. In another aspect of the present invention, the temperature of the effluent stream entering a solids wash is about 5° F. (3° C.) or more above the dew point temperature of the effluent stream, and in yet another aspect of the present invention, the temperature of the effluent entering a solids wash is about 10° F. (5.5° C.) or more above the dew point temperature of the effluent stream. In further embodiments, the temperature of the effluent entering a solids wash ranges from about 1° F. (0.5° C.) to about 400° F. (220° C.) above its dew point temperature, preferably from about 5° F. (3° C.) to about 200° F. (110° C.) above its dew point temperature, more preferably from about 10° F. (5.5° C.) to about 100° F. (55° C.) above its dew point temperature.

In a solids wash, a sufficient quantity of a liquid phase is quickly established that is in contact with the effluent stream such that solid particles, particularly catalyst particles, in the effluent stream are removed from the gas phase of the effluent stream into the liquid phase in the wash device. The "washing" likewise removes the catalyst particles from the solids wash to prevent accumulation of catalyst particles and fouling of the solids wash. This is accomplished when the concentration of solids in a liquid phase (a dilute liquid stream) at any point in the solids wash is dilute enough to prevent mud formation, or dilute enough so that fouling due to mud does not necessitate the shutdown of the solids wash.

In one embodiment of the present invention, the amount of solids removed from the gas phase of the effluent stream into a dilute liquid stream in a solids wash device should be sufficient such that mud does not form in the equipment of the OTO recovery train downstream from the solids wash device. In another embodiment, the amount of solids removed from the gas phase of the effluent stream into a dilute liquid stream in a solids wash device should be sufficient so that it does not necessitate frequent shutdown of equipment in the OTO recovery train downstream of the solids wash device into which prime olefins in the gaseous state is introduced. In one embodiment, about 50 wt % or more of the solids entrained in the effluent stream entering a solids wash device are present in a dilute liquid stream leaving the solids wash device. In other embodiments, about 75 wt % or more, preferably about 95 wt % or more, most preferably 99 wt % or more, of the solids entrained in the effluent stream entering a solids wash device are present in a dilute liquid stream leaving the solids wash device.

A solids wash device of one embodiment establishes a sufficient quantity of a liquid phase in contact with the effluent stream through the introduction of a wash medium. In one embodiment, a wash medium is introduced to a solids wash device at a rate and condition such that a portion of wash medium is vaporized while still forming a sufficient quantity of a liquid phase in contact with effluent stream, and no material in the effluent stream is condensed. In other embodiments, a liquid is introduced into the solids wash device at its bubble point temperature, preferably at temperature of about 1° F. (0.5° C.) below its bubble point temperature or more, more preferably at a temperature of about 5° F. (3° C.) below its bubble point temperature or more, most preferably at about 10° F. (5.5° C.) below its bubble point temperature or more. The bubble point temperature of a liquid is defined as the temperature at which vaporization of any of the components in a liquid first begins, essentially, the converse of the dew point temperature discussed above, with similar attributes regarding its dependencies.

In another embodiment the wash medium introduced in the solids wash device is introduced at a rate and under conditions such that a portion of wash medium is vaporized while still forming a sufficient quantity of a liquid phase in contact with effluent stream.

According to one embodiment, suitable wash media include water, hydrocarbons, (particularly hydrocarbons containing 5 or greater carbon atoms), oxygenated hydrocarbons, and combinations thereof. Water is a particularly effective wash medium.

In still another embodiment of the present invention, a solids wash device establishes a sufficient quantity of a liquid phase in contact with the effluent stream through the introduction of a wash medium which condenses at least a portion of the material in the effluent stream. Such an operation is typically called "quenching," and takes place in a "quench device," and the wash medium is called a "quench medium."

In a quench device, at least a portion of the gaseous effluent stream is rapidly condensed through contact with a quench medium in the liquid state (a form of what is typically called "direct contact heat transfer"). The rapid condensing or "quenching" of some or all of the components in the effluent stream does not cause the formation of mud on surfaces, as a substantial quantity of liquid components are present from both those condensed from the effluent stream and the quench medium itself such that entrained solids, particularly catalyst particles, are separated into a dilute liquid stream in the quench device. The quench device then serves two purposes in a single unit operation, that of washing to separate entrained solids in a dilute liquid stream, and condensing components of the effluent stream, for example water, which in certain applications is beneficial to further processing in the recovery train.

In one embodiment, about 10 wt % or more of the effluent stream is condensed during quenching. In another embodiment about 25 wt % or more of effluent stream is condensed during quenching. In yet another embodiment about 50% or more, and in still another embodiment about 55% or more of the effluent stream is condensed during quenching. According to another embodiment, at least 10% of the water in the effluent stream is condensed during quenching. In another embodiment about 50% or more of the water in the effluent stream is condensed during quenching. In yet another embodiment about 75% or more, and in still another embodiment about 95% or more of the water in the effluent stream is condensed during quenching. When quenching in a quench device, at least a portion of the prime olefins in a gaseous state are separated from the condensed components of the gaseous effluent stream and entrained solids that are then present in a dilute liquid stream.

In one aspect of the present invention, the pressure within a solids wash device, including a quench device, is less than 50 psi (345 kPa) below the pressure at which the effluent stream leaves the OTO reactor and no less than atmospheric pressure. In another aspect, the pressure within the solids wash device, including the quench device, is less than 50 psi (345 kPa) below the pressure at which the effluent stream leaves the OTO reactor and above atmospheric pressure, in yet another aspect it is less than 25 psi (172 kPa) below the pressure at which the effluent stream leaves the OTO reactor and above atmospheric pressure, and in still another aspect it is less than 10 psi (69 kPa) below the pressure at which the effluent stream leaves the OTO reactor and above atmospheric pressure.

According to one embodiment of the present invention, a quench tower is employed as a quench device. In a quench tower, the effluent stream is intimately contacted (i.e., directly exposed in a common volume, and not separated by walls as described above for a heat exchanger) with a quench medium in the liquid state. The quench medium is introduced to the quench tower at a temperature that is both below the quench medium bubble point temperature and the gaseous effluent stream dew point temperature at the lowest pressure within the quench tower. The quench medium is introduced in sufficient volume to cause the effluent stream to move rapidly below its dew point temperature such that a substantial portion of the effluent stream rapidly condenses.

In one embodiment, the temperature of the quench medium is below the quench medium dew point temperature and the aqueous dew point temperature of the effluent stream at the lowest pressure in the quench tower, and causes a substantial portion of the water present in the effluent stream to condense. The quench medium, according to one method of use, is introduced into the quench tower at a location or locations above where the effluent stream is introduced, such that it will fall within the tower and be contacted with the effluent stream as it, or portions of it including the prime olefins in a gaseous state, rise through the tower. The quench tower typically includes internal elements to facilitate the intimate contacting of the quench medium with the reactor effluent or portions thereof, including liquid distributors and contacting devices such as baffles or trays. Intimate contacting with a liquid quench medium facilitates drawing catalyst fines out of the reactor effluent, into a free-flowing, dilute liquid phase and away from at least a portion of the prime olefins in a gaseous state. The quench tower usually also include other elements, such as heat exchangers used to cool the quench medium that is recirculated into the quench tower.

In a particular embodiment, the quench medium is water. In another embodiment, the quench medium is a portion of the water that has been recovered from the quench tower and cooled (thus reintroduced to the quench tower), and which contains at least a portion of the solids separated from the gaseous effluent stream. In one embodiment, the quench medium is a portion of the water that has been recovered from the bottom of the quench tower.

In one embodiment, the temperature of the quench medium introduced to a quench device is at or below its bubble point at the lowest pressure in the quench device. In an alternative embodiment, the temperature of the quench medium introduced to a quench device is 1° F. (0.5° C.) or more below its bubble point at the lowest pressure in the quench device. In further alternatives, the temperature of the quench medium introduced to a quench device is 5° F. (3° C.) or more below its bubble point, preferably 10° F. (5.5° C.) or more below its bubble point, more preferably 50° F. (28° C.) or more below its bubble point, even more preferably 100° F. (55° C.) or more below its bubble point, and yet even more preferably 130° F. (72° C.) or more below its bubble point, and most preferably 150° F. (83° C.) or more below its bubble point, at the lowest pressure in the quench device.

The method and apparatus of the present invention is further understood by reading the following specific examples, which are not intended to limit the scope of the invention is utilized.

EXAMPLE 1

A feed stream containing 99 wt % methanol and 1 wt % water is fed into an OTO reactor containing a SAPO-34 catalyst. The reactor is operated at a temperature of 923° F. (495° C.), a pressure of 40 psia (280 kPa), and a 95% methanol conversion. Components in the effluent stream exiting the OTO reactor, and their flow rates, are shown in Table 1.

TABLE 1

Gaseous Effluent Stream

Vapor, wt %

| | |
|---|---|
| Hydrocarbon & Oxygenates, | 42.5 |
| Water, | 57.5 |
| Total Vapor, | 100.0 |
| Fines, (PPM) | 100 |

Fines Particle Size Distribution (PSD)

| Cumulative wt % Less than | Particle Size Microns |
|---|---|
| 0.01 | 0.1 |
| 1.0 | 0.2 |
| 5.0 | 0.4 |
| 10.0 | 0.5 |
| 30.0 | 0.9 |
| 50.0 | 1.4 |
| 70.0 | 2.9 |
| 90.0 | 16.8 |
| 95.0 | 20.5 |
| 99.0 | 27.1 |

The effluent stream is in the vapor phase, with catalyst fines entrained in the vapor comprising 0.01 wt % of the entire effluent stream. The particle density of the catalyst fines is 75 lb/ft$_3$ (1.2 g/cc).

Figure 1:
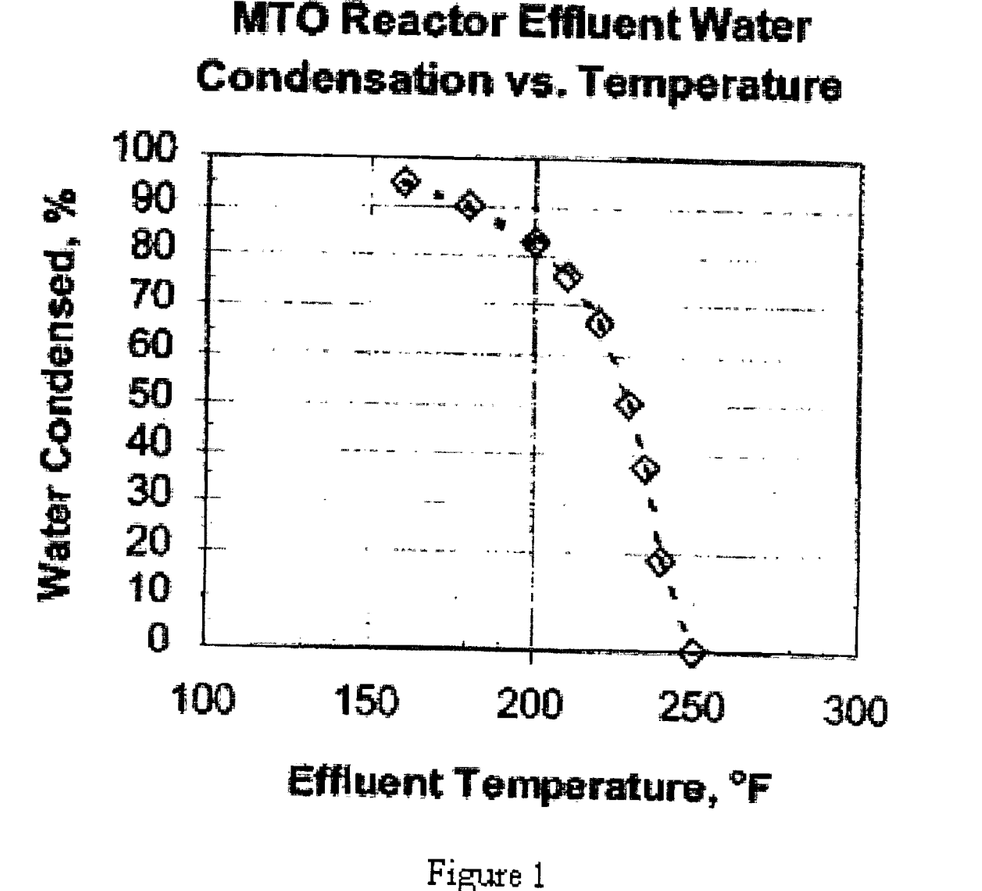
FIG. 1 is a graphic representation of Water Condensation vs. Temperature of the Effluent Stream of a Methanol to Olefin Reaction at 40 psia.

FIG. 1 shows the percent of condensed water in the effluent stream versus temperature at 40 psia (280 kPa).

In heat exchangers and other equipment downstream from the reactor prior to a quench device, the pressure is maintained at about 40 psia (280 kPa), but the temperature of the effluent stream falls below its dew point temperature of about 250° F. (120° C.), as shown in FIG. 1. Small quantities of water in the effluent stream will condense incrementally along the surfaces of the downstream equipment below the dew point temperature, wetting the surfaces of process equipment. The catalyst fines in the effluent stream adhere to the wet surfaces forming appreciable quantities of mud. The formation of mud in heat exchangers and other equipment decreases their effectiveness and reliability.

EXAMPLE 2

The gaseous effluent stream described in Table 1 is conveyed to a quench device at about 40 psia (280 kPa). FIG. 1 shows that with an OTO effluent stream given in Table 1, the condensation of water is prevented by keeping the temperature of the effluent stream above about 250° F. (120° C.) while it is being conveyed to a quench device. Therefore, the temperature of the effluent stream is dropped down to a temperature of 250° F. (120° C.) without mud forming in equipment prior to entering the quench device. The effluent stream then enters the quench device operating at a pressure of about 40 psia and is quenched to rapidly cool the effluent stream to 200° F. (93° C.) causing more than about 80% of the water in the effluent stream to condense. The catalyst fines leave the remaining gas phase of the effluent stream and enter the dilute liquid phase of the condensed water. Since there is a large amount of condensed water relative to the amount of catalyst fines, mud is not formed in the quench device. Prime olefins from the gaseous effluent stream remain in a gaseous state and are separated from the dilute liquid phase comprising primarily condensed water and catalyst fines.

While the invention has been illustrated an described herein in terms of the advantages, features, and applications disclosed, it will be apparent to a person of ordinary skill in the art that the invention can be used in other instances. Other modifications and improvements can be made without departing from the scope of the invention.

What is claimed is:

1. A process for controlling accumulation of catalyst solids in a recovery train of an oxygenate to olefin process comprising:
   providing an effluent stream from an oxygenate to olefin reaction, wherein the effluent stream comprises solid particles and a gas phase containing prime olefins and having a dew point;
   removing heat from the effluent stream while maintaining the effluent stream above the dew point of the gas phased; and
   washing the effluent stream at a temperature below the dew point of the gas phase to remove the solid particles from effluent stream into a wash medium.

2. The process of claim 1, wherein the effluent stream comprises prime olefins in an amount of about 40 wt % or more of the effluent stream excluding water and solid particles.

3. The process of claim 1, wherein the effluent stream comprises prime olefins in an amount of about 60 wt % or more of the effluent stream excluding water and solid particles.

4. The process of claim 1, wherein the effluent stream comprises ethylene in an amount of about 20 wt % or more of the effluent stream excluding water and solid particles.

5. The process of claim 1, wherein the effluent stream comprises ethylene in an amount ranging from about 20 wt % to about 70 wt % of the effluent stream excluding water and solid particles.

6. The process of claim 1, wherein the effluent stream comprises propylene in an amount of about 20 wt % or more of the effluent stream excluding water and solid particles.

7. The process of claim 1, wherein the effluent stream comprises propylene in an amount ranging from about 20 wt % to about 70 wt % of the effluent stream excluding water and solid particles.

8. The process of claim 1, wherein the effluent stream comprises water in an amount of 25 wt % or more of the effluent stream.

9. The process of claim 1, wherein the effluent stream comprises water in an amount ranging from about 40 wt % to about 80 wt % of the effluent stream.

10. The process of claim 1, wherein the effluent stream comprises water in an amount ranging from about 50 wt % to about 65 wt % of the effluent stream.

11. The process of claim 1, wherein the effluent stream comprises oxygenated hydrocarbons in an amount ranging from about 0.2 wt % to about 30 wt % of the effluent stream excluding water and solid particles.

12. The process of claim 1, wherein the effluent stream comprises solid particles in an amount of about 0.15 wt % or less of the effluent stream.

13. The process of claim 1, wherein the effluent stream comprises solid particles in an amount of about 0.010 wt % or less of the effluent stream.

14. The process of claim 1, wherein the effluent stream comprises catalyst particles in an amount ranging from about 0.001 Wt % to about 0.5 wt % of the effluent stream.

15. The process of claim 1, wherein the effluent stream comprises catalyst particles in an amount ranging from about 0.003 wt % to about 0.10 wt % of the effluent stream.

16. The process of claim 1, wherein the effluent stream comprises catalyst particles in an amount ranging from about 0.005 wt % to about 0.05 wt % of the effluent stream.

17. The process of claim 1, wherein the effluent stream has an effluent temperature of about 200° C. or more.

18. The process of claim 1, wherein the effluent stream has an effluent temperature ranging from about 200° C. to about 700° C.

19. The process of claim 1, wherein the effluent stream has an effluent temperature ranging from about 300° C. to about 600° C.

20. The process of claim 1, wherein the effluent stream has an effluent temperature ranging from 350° C. to about 550° C.

21. The process of claim 1 wherein the effluent stream comprises water and hydrocarbons and has an aqueous dew point and a non-aqueous dew point, the aqueous dew point being higher than the non-aqueous dew point.

22. The process for claim 1, wherein the step of removing heat comprises removing heat with one or more heat exchanger.

23. The process of claim 22, wherein the temperature of the effluent stream is maintained at a temperature of about 3° C. above the dew point prior to the step of washing.

24. The process of claim 22, wherein the temperature of the effluent stream is maintained at a temperature of about 5.5° C. above the dew point prior to the step of washing.

25. The process of claim 22, wherein the temperature of the effluent stream is maintained at a temperature of about 10° C. above the dew point prior to the step of washing.

26. The process of claim 22, wherein the oxygenate to olefins reaction occurs in a reactor, the reactor being in fluid communication with the one or more heat exchangers and the solids wash by a conduit.

27. The process of claim 22, wherein the step of providing an effluent stream further comprises:
providing a feed stream to the oxygenate to olefin reactor, wherein the feed stream is used as a cooling fluid in the heat exchanger.

28. The process for claim 27, wherein the cooling fluid is boiled within the heat exchanger.

29. The process of claim 1, wherein the wash medium is water.

30. The process of claim 1, wherein the solids wash is a quench tower.

31. A process for producing olefins, the process comprising the steps of:
providing an oxygenate feed stream;
reacting the oxygenate feed stream in the presence of a catalyst to produce an effluent stream, wherein the effluent stream has a dew point and comprises an olefin containing gas phase and catalyst solids;
removing heat from the effluent stream while maintaining the temperature of the effluent stream above the dew point of the gas phase; and
contacting the effluent stream with a liquid at a temperature below the dew point of the gas phase; and
separating the catalyst solids from the olefin containing gas phase.

32. The process of claim 31, wherein the oxygenate feed stream contains methanol.

33. The process of claim 32, wherein the catalyst is a molecular sieve catalyst.

34. The process of claim 33, wherein the molecular sieve catalyst comprises a silicoaluminophosphate molecular sieve selected from SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, or mixtures thereof.

35. The process of claim 31, wherein the step of contacting occurs in a quench tower.

36. The process of claim 31, wherein the step of removing heat is accomplished using a heat exchanger.

37. The process of claim 36, wherein the oxygenate feed stream is used as a cooling fluid in the heat exchanger.

38. The process of claim 37, wherein the oxygenate feed is boiled in the step of removing heat.

39. The process of claim 31, wherein the step of reacting occurs at a temperature ranging from about 200° C. to about 700° C. and an oxygenate partial pressure of about 1 psia or more.

40. The process for claim 31, wherein the step of reacting occurs at a temperature ranging from about 350° C. to about 550° C. and an oxygenate partial pressure of about 1 psia or more.

41. The process for claim 31, wherein the step of reacting occurs at a temperature ranging from about 200° C. to about 700° C. and an oxygenate partial pressure of greater than or equal to 20 psia.

42. The process for claim 31, wherein the step of reacting occurs at a temperature ranging from about 300° C. to about 600° C. and an oxygenate partial pressure of greater than or equal to about 20 psia.

43. The process for claim 31, wherein the step of reacting occurs at a temperature ranging from about 350° C. to about 550° C. and an oxygenate partial pressure of greater than or equal to about 20 psia.

44. A process for producing olefins, the process comprising the steps of:
providing an oxygenate feed stream;
reacting the oxygenate feed stream in the presence of a catalyst to produce a product stream containg catalyst and olefin;
separating catalyst from the product stream in a cyclone separator to produce an effluent stream comprising an olefin containing gas phase and catalyst lines;
removing heat from the effluent stream at a temperature that remains above the dew point of the effluent stream to provide a cooled effluent stream; and
washing catalyst fines from the cooled effluent stream in a wash to remove the catalyst fines from the olefin containing gas phase.

* * * * *

(12) INTER PARTES REEXAMINATION CERTIFICATE (670th)
United States Patent
Lumgair et al.

(10) Number: US 6,870,072 C1
(45) Certificate Issued: Aug. 16, 2013

(54) HEAT RECOVERY IN AN OLEFIN PRODUCTION PROCESS

(75) Inventors: David R Lumgair, Craddockville, VA (US); James Harding Beech, Kingwood, TX (US)

(73) Assignee: ExxonMobil Chemical Patents Inc., Houston, TX (US)

Reexamination Request:
No. 95/001,387, Jul. 12, 2010

Reexamination Certificate for:
Patent No.: 6,870,072
Issued: Mar. 22, 2005
Appl. No.: 10/020,732
Filed: Oct. 30, 2001

(51) Int. Cl.
*C07C 1/20* (2006.01)
*C07C 1/00* (2006.01)
*C07C 11/02* (2006.01)

(52) U.S. Cl.
USPC ........... 585/639; 208/161; 585/634; 585/640; 585/910; 585/911

(58) Field of Classification Search
None
See application file for complete search history.

(56) References Cited

To view the complete listing of prior art documents cited during the proceeding for Reexamination Control Number 95/001,387, please refer to the USPTO's public Patent Application Information Retrieval (PAIR) system under the Display References tab.

*Primary Examiner* — Alan Diamond (57) ABSTRACT

Disclosed is a process for recovering heat in an oxygenate to olefin ("OTO") production process. The process includes removing heat while maintaining the temperature of an effluent stream that comprises solid particles (typically catalyst particles) and a gas phase comprising prime olefins from an OTO reactor above the dew point temperature of the effluent stream. The process further includes washing the effluent stream in solids wash to remove the solid particles from the gas phase into a liquid wash medium.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-44 are cancelled.

\* \* \* \* \*